United States Patent
Fujikawa

(10) Patent No.: US 12,087,416 B2
(45) Date of Patent: Sep. 10, 2024

(54) HEALTH MANAGEMENT SYSTEM

(71) Applicant: F&F INC., Tochigi (JP)

(72) Inventor: Yoshihiro Fujikawa, Tochigi (JP)

(73) Assignee: F&F INC., Tochigi (JP)

( * ) Notice: Subject to any disclaimer, the term of this patent is extended or adjusted under 35 U.S.C. 154(b) by 0 days.

(21) Appl. No.: 18/278,997

(22) PCT Filed: Jun. 22, 2021

(86) PCT No.: PCT/JP2021/023555
§ 371 (c)(1),
(2) Date: Aug. 25, 2023

(87) PCT Pub. No.: WO2022/185554
PCT Pub. Date: Sep. 9, 2022

(65) Prior Publication Data
US 2024/0038350 A1    Feb. 1, 2024

(30) Foreign Application Priority Data
Mar. 2, 2021 (JP) .................. 2021-032380

(51) Int. Cl.
*G16H 20/00* (2018.01)
*G06F 21/32* (2013.01)
(Continued)

(52) U.S. Cl.
CPC ............ *G16H 20/00* (2018.01); *G06F 21/32* (2013.01); *G16H 10/60* (2018.01); *G16H 40/67* (2018.01)

(58) Field of Classification Search
CPC ........ G16H 10/60; G16H 20/00; G16H 40/67; G06F 21/00; G06F 21/32
(Continued)

(56) References Cited

U.S. PATENT DOCUMENTS 5,410,471 A     4/1995  Alyfuku et al.
10,667,759 B2   6/2020  Duke et al.
(Continued)

FOREIGN PATENT DOCUMENTS

CN     104850758 A    8/2015
JP       3144030 B2    3/2001
(Continued)

OTHER PUBLICATIONS

Christiansen, Kathryn Ellen; the Determinants of Health Promoting Behavior; Rush University, College of Nursing. ProQuest Dissertation & Theses, 1981. 8314063 (Year: 1981).*
(Continued)

*Primary Examiner* — Hiep V Nguyen
(74) *Attorney, Agent, or Firm* — Paratus Law Group, PLLC

(57) ABSTRACT

A healthcare system measures each item related to health; calculates an evaluation value from the measured measurement value, the evaluation value being classified into evaluation classifications of a standard evaluation, a positive evaluation, and a negative evaluation; sets the importance of an inspection result for each measurement item; selects a predetermined number of items in descending order of a weight of the importance and in which the classification is the negative evaluation; generates an inspection result from contents of the evaluation classification of the selected item; and determines and notifies the advice contents according to the inspection result, the notification being performed on a printed matter or a screen of a mobile terminal.

7 Claims, 10 Drawing Sheets

(51) Int. Cl.
*G16H 10/60* (2018.01)
*G16H 40/67* (2018.01)

(58) Field of Classification Search
USPC .............................................................. 705/2
See application file for complete search history.

(56) References Cited

U.S. PATENT DOCUMENTS

| | | | |
|---|---|---|---|
| 11,495,335 B2 * | 11/2022 | Sano | ...................... G16H 40/20 |
| 2002/0169634 A1 | 11/2002 | Nishi et al. | |
| 2007/0276270 A1 | 11/2007 | Tran | |
| 2014/0324443 A1 | 10/2014 | Ricks et al. | |
| 2017/0049963 A1 | 2/2017 | Varsavsky et al. | |
| 2018/0020968 A1 | 1/2018 | Djajadiningrat et al. | |
| 2018/0096739 A1 * | 4/2018 | Sano | ...................... G06F 16/316 |
| 2018/0271455 A1 | 9/2018 | Zhong et al. | |
| 2018/0344239 A1 | 12/2018 | Blander et al. | |
| 2020/0258637 A1 | 8/2020 | Jain et al. | |

FOREIGN PATENT DOCUMENTS

| | | | | |
|---|---|---|---|---|
| JP | 2015-111438 A | | 6/2015 | |
| JP | 6615493 B2 * | | 12/2019 | ......... A61B 10/0012 |
| JP | 6762061 B1 | | 9/2020 | |
| WO | WO 02/051308 A1 | | 7/2002 | |
| WO | WO-2016190210 A1 * | | 12/2016 | ......... A61B 10/0012 |
| WO | WO 2020/091053 A1 | | 5/2020 | |

OTHER PUBLICATIONS

Aug. 10, 2021, International Search Report issued for related PCT Application No. PCT/JP2021/023555.
Aug. 10, 2021, International Search Opinion issued for related PCT Application No. PCT/JP2021/023555.
May 31, 2022, Japanese Notice of Reasons for Refusal issued for related JP Application No. 2021-032380.
Oct. 11, 2022, Japanese Decision to Grant a Patent issued for related JP Application No. 2021-032380.
Nov. 1, 2023, Australian Office Action issued for related AU Application No. 2021430628.
Ganesh et al., AutoImpilo: Smart Automated Health Machine using IoT to Improve Telemedicine and Telehealth, IEEE, 2020, pp. 487-493.
Dec. 27, 2023, Canadian Office Action issued for related CA Application No. 3,211,965.
Apr. 24, 2024, Chinese Office Action issued for related CN Application No. 202180094996.5.
May 28, 2024, European Search Report issued for related EP Application No. 21929125.9.

* cited by examiner

FIG. 2

| AGE | GENDER | WEIGHT | | | | | |
| --- | --- | --- | --- | --- | --- | --- | --- |
| | | BLOOD VESSEL AGE | BONE DENSITY | AGEs | BODY COMPOSITION ANALYSIS | FORGETFULNESS | SKIN AGE |
| 29 YEARS OLD OR LESS | MALE | 30% | 20% | 15% | 25% | 5% | 5% |
| | FEMALE | 30% | 5% | 15% | 20% | 5% | 25% |
| 30 TO 49 YEARS OLD | MALE | 30% | 15% | 20% | 25% | 5% | 5% |
| | FEMALE | 30% | 20% | 5% | 20% | 5% | 25% |
| 50 TO 69 YEARS OLD | MALE | 30% | 25% | 20% | 15% | 5% | 5% |
| | FEMALE | 25% | 30% | 20% | 15% | 5% | 5% |
| 70 YEARS OLD OR MORE | MALE | 30% | 25% | 20% | 5% | 15% | 5% |
| | FEMALE | 25% | 30% | 20% | 5% | 15% | 5% |

T10 T11 INDIVIDUAL WEIGHT-SETTING TABLE

FIG. 3

| INSPECTION ITEM | INSPECTION ITEM IDENTIFICATION SYMBOL | WEIGHT FOR EACH INSPECTION (%) | DETERMINATION ITEM/ABNORMALITY LINE | DISTRIBUTED POINT-CORRESPONDING CHARACTER STRING ||||||
|---|---|---|---|---|---|---|---|---|---|
| | | | | NEGATIVE EVALUATION ||| STANDARD | POSITIVE EVALUATION ||
| BLOOD VESSEL AGE | A | 30% | POINTS (OUT OF 100 POINTS) LESS THAN 40 POINTS | 19 OR LESS | 20~29 | 30~39 | 40~59 | 60~79 | 80~100 |
| | | | | a | b | c | d | e | f |
| BONE DENSITY | B | 25% | T SCORE (COMPARED WITH 20 YEARS OLD) -1 OR MORE | -2.5 SD OR MORE | -2.4~ -1.5D | -1.4~ -1SD | ±0~2 | +3~4 | +5 OR MORE |
| | | | | g | h | i | j | k | l |
| AGEs | C | 20% | 5 LEVELS OF EVALUATION (A TO E) C OR LESS | E | D | C | B | A | A+ |
| | | | | m | n | o | p | q | r |
| BODY COMPOSITION ANALYSIS | D | 15% | POINTS (OUT OF 100 POINTS) | 49 OR LESS | 50~59 | 60~74 | 75~80 | 80~90 | 90~100 |
| | | | 80 POINTS OR LESS FAT (LESS) MUSCLE (LESS) | s | t | u | v | w | x |
| | | | 80 POINTS OR LESS FAT (MORE) MUSCLE (LESS) | y | z | aa | ab | ac | ad |
| | | | 80 POINTS OR LESS FAT (MORE) MUSCLE (MORE) | ae | af | ag | ah | ai | aj |
| FORGETFU-LNESS | E | 5% | POINTS (OUT OF 15 POINTS) LESS THAN 13 POINTS | 10 | 11 | 12 | 13 | 14 | 15 |
| | | | | ak | al | am | an | ao | ap |
| SKIN AGE | F | 5% | 5 LEVELS OF EVALUATION (A TO E) D OR LESS | E- | E | D | C | B | A |
| | | | | aq | ar | as | at | av | aw |

T20  RELATION TABLE BETWEEN MEASUREMENT VALUE AND EVALUATION

FIG. 4A

| INSPECTION ITEM | INSPECTION ITEM IDENTIFICATION SYMBOL | WEIGHT WITH RESPECT TO RESULT (%) | DETERMINATION ITEM/ABNORMALITY LINE | CORRESPONDING CHARACTER STRING ||||| 
|---|---|---|---|---|---|---|---|---|
| | | | | NEGATIVE EVALUATION || STANDARD | POSITIVE EVALUATION ||
| BLOOD VESSEL AGE | A | 30% | | a | b | c | d | e | f |
| BONE DENSITY | B | 25% | | g | h | i | j | k | l |
| AGEs | C | 20% | | m | n | o | p | q | r |
| BODY COMPOSITION ANALYSIS | D | 15% | FAT (LESS) MUSCLE (LESS) | s | t | u | v | w | x |
| | | | FAT (MORE) MUSCLE (LESS) | y | z | aa | ab | ac | ad |
| | | | FAT (MORE) MUSCLE (MORE) | ae | af | ag | ah | ai | aj |
| FORGETFULNESS | E | 5% | | ak | al | am | an | ao | ap |
| SKIN AGE | F | 5% | | aq | ar | as | at | av | aw |

SELECTION EXAMPLE OF EVALUATION CHARACTER STRING

FIG. 4B

| INSPECTION ITEM | INSPECTION ITEM IDENTIFICATION SYMBOL | WEIGHT WITH RESPECT TO RESULT (%) | DETERMINATION ITEM/ABNORMALITY LINE | CORRESPONDING CHARACTER STRING ||||| 
|---|---|---|---|---|---|---|---|---|
| | | | | NEGATIVE EVALUATION || STANDARD | POSITIVE EVALUATION ||
| BLOOD VESSEL AGE | A | 30% | | a | b | c | d | e | f |
| BONE DENSITY | B | 25% | | g | h | i | j | k | l |
| AGEs | C | 20% | | m | n | o | p | q | r |
| BODY COMPOSITION ANALYSIS | D | 15% | FAT (LESS) MUSCLE (LESS) | s | t | u | v | w | x |
| | | | FAT (MORE) MUSCLE (LESS) | y | z | aa | ab | ac | ad |
| | | | FAT (MORE) MUSCLE (MORE) | ae | af | ag | ah | ai | aj |
| FORGETFULNESS | E | 5% | | ak | al | am | an | ao | ap |
| SKIN AGE | F | 5% | | aq | ar | as | at | av | aw |

SELECTION EXAMPLE OF EVALUATION CHARACTER STRING

FIG. 5

| EVALUATION RESULT | | | PATTERN | ADVICE CONTENTS | |
|---|---|---|---|---|---|
| Aa | Bg | Cm | 1 | PAY ATTENTION TO BLOOD VESSEL AGE | PAY ATTENTION TO BONE DENSITY · PAY ATTENTION TO AGEs |
| Aa | Bg | Cn | 2 | PAY ATTENTION TO BLOOD VESSEL AGE | PAY ATTENTION TO BONE DENSITY · AGEs (MODERATE TO MILD) |
| Aa | Bg | Co | 2 | PAY ATTENTION TO BLOOD VESSEL AGE | PAY ATTENTION TO BONE DENSITY · AGEs (MODERATE TO MILD) |
| Aa | Bh | Cm | 3 | PAY ATTENTION TO BLOOD VESSEL AGE | BONE DENSITY (MODERATE TO MILD) · PAY ATTENTION TO AGEs |
| Aa | Bh | Cn | 4 | PAY ATTENTION TO BLOOD VESSEL AGE | BONE DENSITY (MODERATE TO MILD) · AGEs (MODERATE TO MILD) |
| Aa | Bh | Co | 4 | PAY ATTENTION TO BLOOD VESSEL AGE | BONE DENSITY (MODERATE TO MILD) · AGEs (MODERATE TO MILD) |
| Aa | Bi | Cm | 5 | PAY ATTENTION TO BLOOD VESSEL AGE | BONE DENSITY (MODERATE TO MILD) · PAY ATTENTION TO AGEs |
| Aa | Bi | Cn | 4 | PAY ATTENTION TO BLOOD VESSEL AGE | BONE DENSITY (MODERATE TO MILD) · AGEs (MODERATE TO MILD) |
| Aa | Bi | Co | 4 | PAY ATTENTION TO BLOOD VESSEL AGE | BONE DENSITY (MODERATE TO MILD) · AGEs (MODERATE TO MILD) |
| Ab | Bg | Cm | 6 | BLOOD VESSEL AGE (MODERATE) | PAY ATTENTION TO BONE DENSITY · PAY ATTENTION TO AGEs |
| Ab | Bg | Cn | 7 | BLOOD VESSEL AGE (MODERATE) | PAY ATTENTION TO BONE DENSITY · AGEs (MODERATE TO MILD) |
| Ab | Bg | Co | 7 | BLOOD VESSEL AGE (MODERATE) | PAY ATTENTION TO BONE DENSITY · AGEs (MODERATE TO MILD) |
| Ab | Bh | Cm | 8 | BLOOD VESSEL AGE (MODERATE) | BONE DENSITY (MODERATE TO MILD) · PAY ATTENTION TO AGEs |
| Ab | Bh | Cn | 7 | BLOOD VESSEL AGE (MODERATE) | BONE DENSITY (MODERATE TO MILD) · AGEs (MODERATE TO MILD) |
| Ab | Bh | Co | 7 | BLOOD VESSEL AGE (MODERATE) | BONE DENSITY (MODERATE TO MILD) · AGEs (MODERATE TO MILD) |
| Ab | Bi | Cm | 8 | BLOOD VESSEL AGE (MODERATE) | BONE DENSITY (MODERATE TO MILD) · PAY ATTENTION TO AGEs |
| Ab | Bi | Cn | 7 | BLOOD VESSEL AGE (MODERATE) | BONE DENSITY (MODERATE TO MILD) · AGEs (MODERATE TO MILD) |
| Ab | Bi | Co | 7 | BLOOD VESSEL AGE (MODERATE) | BONE DENSITY (MODERATE TO MILD) · AGEs (MODERATE TO MILD) |
| Ac | Bg | Cm | 9 | BLOOD VESSEL AGE (MILD) | PAY ATTENTION TO BONE DENSITY · PAY ATTENTION TO AGEs |
| Ac | Bg | Cn | 10 | BLOOD VESSEL AGE (MILD) | PAY ATTENTION TO BONE DENSITY · AGEs (MODERATE TO MILD) |
| Ac | Bg | Co | 10 | BLOOD VESSEL AGE (MILD) | PAY ATTENTION TO BONE DENSITY · AGEs (MODERATE TO MILD) |
| Ac | Bh | Cm | 11 | BLOOD VESSEL AGE (MILD) | BONE DENSITY (MODERATE TO MILD) · PAY ATTENTION TO AGEs |
| Ac | Bh | Cn | 12 | BLOOD VESSEL AGE (MILD) | BONE DENSITY (MODERATE TO MILD) · AGEs (MODERATE TO MILD) |
| Ac | Bh | Co | 12 | BLOOD VESSEL AGE (MILD) | BONE DENSITY (MODERATE TO MILD) · AGEs (MODERATE TO MILD) |
| Ac | Bi | Cm | 11 | BLOOD VESSEL AGE (MILD) | BONE DENSITY (MODERATE TO MILD) · PAY ATTENTION TO AGEs |
| Ac | Bi | Cn | 12 | BLOOD VESSEL AGE (MILD) | BONE DENSITY (MODERATE TO MILD) · AGEs (MODERATE TO MILD) |
| Ac | Bi | Co | 12 | BLOOD VESSEL AGE (MILD) | BONE DENSITY (MODERATE TO MILD) · AGEs (MODERATE TO MILD) |

RELATION TABLE BETWEEN EVALUATION CHARACTER STRING AND PATTERN NUMBER

FIG. 6

| PATTERN | ADVICE CONTENTS | | | RELATED VIDEO | RELATED SITE AND HP |
|---|---|---|---|---|---|
| 1 | PAY ATTENTION TO BLOOD VESSEL AGE | PAY ATTENTION TO BONE DENSITY | PAY ATTENTION TO AGEs | VIDEO A GENERAL LIFE GUIDANCE | SITE A (OVERALL MEDICAL DIET SITE) |
| 2 | PAY ATTENTION TO BLOOD VESSEL AGE | PAY ATTENTION TO BONE DENSITY | AGEs (MODERATE TO MILD) | VIDEO B (EXERCISE THERAPY VIDEO) | SITE B (CHOLESTEROL REDUCTION MEDICAL DIET SITE) |
| 3 | PAY ATTENTION TO BLOOD VESSEL AGE | BONE DENSITY (MODERATE TO MILD) | PAY ATTENTION TO AGEs | VIDEO B (EXERCISE THERAPY VIDEO) | SITE B (CHOLESTEROL REDUCTION MEDICAL DIET SITE) |
| 4 | PAY ATTENTION TO BLOOD VESSEL AGE | BONE DENSITY (MODERATE TO MILD) | AGEs (MODERATE TO MILD) | VIDEO B (EXERCISE THERAPY VIDEO) | SITE B (CHOLESTEROL REDUCTION MEDICAL DIET SITE) |
| 5 | PAY ATTENTION TO BLOOD VESSEL AGE | BONE DENSITY (MODERATE TO MILD) | PAY ATTENTION TO AGEs | VIDEO B (EXERCISE THERAPY VIDEO) | SITE B (CHOLESTEROL REDUCTION MEDICAL DIET SITE) |
| 6 | BLOOD VESSEL AGE (MODERATE) | PAY ATTENTION TO BONE DENSITY | PAY ATTENTION TO AGEs | VIDEO C (MILD EXERCISE THERAPY VIDEO) | SITE C (MINERAL AND OXIDATION REDUCTION MEDICAL DIET SITE) |
| 7 | BLOOD VESSEL AGE (MODERATE) | BONE DENSITY (MODERATE TO MILD) | AGEs (MODERATE TO MILD) | VIDEO C (MILD EXERCISE THERAPY VIDEO) | SITE C (MINERAL AND OXIDATION REDUCTION MEDICAL DIET SITE) |
| 8 | BLOOD VESSEL AGE (MODERATE) | BONE DENSITY (MODERATE TO MILD) | PAY ATTENTION TO AGEs | VIDEO C (MILD EXERCISE THERAPY VIDEO) | SITE C (MINERAL AND OXIDATION REDUCTION MEDICAL DIET SITE) |
| 9 | BLOOD VESSEL AGE (MILD) | PAY ATTENTION TO BONE DENSITY | PAY ATTENTION TO AGEs | VIDEO D (PHYSICAL MAINTENANCE THERAPY VIDEO) | SITE D (HEALTH PROMOTION MEDICAL DIET SITE) |
| 10 | BLOOD VESSEL AGE (MILD) | PAY ATTENTION TO BONE DENSITY | AGEs (MODERATE TO MILD) | VIDEO D (PHYSICAL MAINTENANCE THERAPY VIDEO) | SITE D (HEALTH PROMOTION MEDICAL DIET SITE) |
| 11 | BLOOD VESSEL AGE (MILD) | BONE DENSITY (MODERATE TO MILD) | PAY ATTENTION TO AGEs | VIDEO D (PHYSICAL MAINTENANCE THERAPY VIDEO) | SITE D (HEALTH PROMOTION MEDICAL DIET SITE) |
| 12 | BLOOD VESSEL AGE (MILD) | BONE DENSITY (MODERATE TO MILD) | AGEs (MODERATE TO MILD) | VIDEO D (PHYSICAL MAINTENANCE THERAPY VIDEO) | SITE D (HEALTH PROMOTION MEDICAL DIET SITE) |

RELATION TABLE BETWEEN PATTERN NUMBER AND VIDEO AND SITE

FIG. 9

| EVALUATION RESULT | | | PATTERN | ADVICE CONTENTS | | |
|---|---|---|---|---|---|---|
| Aa | Bi | Cp | 101 | PAY ATTENTION TO BLOOD VESSEL AGE | BONE DENSITY STANDARD | AGEs STANDARD |
| Aa | Bi | Cq | 102 | PAY ATTENTION TO BLOOD VESSEL AGE | BONE DENSITY STANDARD | LESS MAINTAIN AGEs |
| Aa | Bj | Cr | 102 | PAY ATTENTION TO BLOOD VESSEL AGE | BONE DENSITY STANDARD | LESS MAINTAIN AGEs |
| Aa | Bk | Cp | 103 | PAY ATTENTION TO BLOOD VESSEL AGE | RECOMMENDED TO MAINTAIN BONE DENSITY | AGEs STANDARD |
| Aa | Bk | Cq | 104 | PAY ATTENTION TO BLOOD VESSEL AGE | RECOMMENDED TO MAINTAIN BONE DENSITY | LESS MAINTAIN AGEs |
| Aa | Bk | Cr | 104 | PAY ATTENTION TO BLOOD VESSEL AGE | RECOMMENDED TO MAINTAIN BONE DENSITY | LESS MAINTAIN AGEs |
| Aa | Bl | Cp | 105 | PAY ATTENTION TO BLOOD VESSEL AGE | RECOMMENDED TO MAINTAIN BONE DENSITY | AGEs STANDARD |
| Aa | Bl | Cq | 104 | PAY ATTENTION TO BLOOD VESSEL AGE | RECOMMENDED TO MAINTAIN BONE DENSITY | LESS MAINTAIN AGEs |
| Aa | Bl | Cr | 104 | PAY ATTENTION TO BLOOD VESSEL AGE | RECOMMENDED TO MAINTAIN BONE DENSITY | LESS MAINTAIN AGEs |
| Ab | Bj | Cp | 106 | BLOOD VESSEL AGE (MODERATE) | BONE DENSITY STANDARD | AGEs STANDARD |
| Ab | Bj | Cq | 107 | BLOOD VESSEL AGE (MODERATE) | BONE DENSITY STANDARD | LESS MAINTAIN AGEs |
| Ab | Bj | Cr | 107 | BLOOD VESSEL AGE (MODERATE) | BONE DENSITY STANDARD | LESS MAINTAIN AGEs |
| Ab | Bk | Cp | 108 | BLOOD VESSEL AGE (MODERATE) | RECOMMENDED TO MAINTAIN BONE DENSITY | AGEs STANDARD |
| Ab | Bk | Cq | 107 | BLOOD VESSEL AGE (MODERATE) | RECOMMENDED TO MAINTAIN BONE DENSITY | LESS MAINTAIN AGEs |
| Ab | Bk | Cr | 108 | BLOOD VESSEL AGE (MODERATE) | RECOMMENDED TO MAINTAIN BONE DENSITY | LESS MAINTAIN AGEs |
| Ab | Bl | Cp | 107 | BLOOD VESSEL AGE (MODERATE) | RECOMMENDED TO MAINTAIN BONE DENSITY | AGEs STANDARD |
| Ab | Bl | Cq | 107 | BLOOD VESSEL AGE (MODERATE) | RECOMMENDED TO MAINTAIN BONE DENSITY | LESS MAINTAIN AGEs |
| Ac | Bj | Cp | 109 | BLOOD VESSEL AGE (MILD) | BONE DENSITY STANDARD | AGEs STANDARD |
| Ac | Bj | Cq | 110 | BLOOD VESSEL AGE (MILD) | BONE DENSITY STANDARD | LESS MAINTAIN AGEs |
| Ac | Bj | Cr | 110 | BLOOD VESSEL AGE (MILD) | BONE DENSITY STANDARD | LESS MAINTAIN AGEs |
| Ac | Bk | Cp | 110 | BLOOD VESSEL AGE (MILD) | RECOMMENDED TO MAINTAIN BONE DENSITY | AGEs STANDARD |
| Ac | Bk | Cq | 112 | BLOOD VESSEL AGE (MILD) | RECOMMENDED TO MAINTAIN BONE DENSITY | LESS MAINTAIN AGEs |
| Ac | Bk | Cr | 112 | BLOOD VESSEL AGE (MILD) | RECOMMENDED TO MAINTAIN BONE DENSITY | LESS MAINTAIN AGEs |
| Ac | Bl | Cp | 111 | BLOOD VESSEL AGE (MILD) | RECOMMENDED TO MAINTAIN BONE DENSITY | AGEs STANDARD |
| Ac | Bl | Cq | 112 | BLOOD VESSEL AGE (MILD) | RECOMMENDED TO MAINTAIN BONE DENSITY | LESS MAINTAIN AGEs |
| Ac | Bl | Cr | 112 | BLOOD VESSEL AGE (MILD) | RECOMMENDED TO MAINTAIN BONE DENSITY | LESS MAINTAIN AGEs |

T50 MODIFICATION OF RELATION TABLE BETWEEN EVALUATION CHARACTER STRING AND PATTERN NUMBER

T51

HEALTH MANAGEMENT SYSTEM

CROSS REFERENCE TO PRIOR APPLICATION

This application is a National Stage Patent Application of PCT International Patent Application No. PCT/JP2021/023555 (filed on Jun. 22, 2021) under 35 U.S.C. § 371, which claims priority to Japanese Patent Application No. 2021-032380 (filed on Mar. 2, 2021), which are all hereby incorporated by reference in their entirety.

TECHNICAL FIELD

The present invention relates to a health management system (a healthcare system), and more particularly to a technique of a healthcare system capable of providing a user with accurate information in an easy-to-understand manner.

BACKGROUND ART

In the related art, as a method of grasping and guiding a health condition of an individual, a system is developed in which contents of individual advice and advice as a whole are notified from a value and an index of each measurement device. In addition, a method of setting points as a result of a measurement device to sort which advice is to be guided based on a total value is also executed.

However, even if a numerical value of the total value is the same, there is a person who needs advice on a blood vessel age, and there is also a person who needs advice on AGEs. Depending on an attribute of the individual, a measurement item that is not important is present, and an item that has little influence on health of the individual is also present. When advice including these items is given, advice contents may be complicated and difficult to understand. Therefore, a system that advises on an item having high importance and high necessity for advice for each individual is required.

In order to solve such a problem, various techniques are proposed in the related art. For example, a system is described in which a health condition of an individual is captured by a sensor or the like, input to a controller, and managed for each individual (see Patent Literature 1). In addition, a healthcare apparatus for acquiring health-related information of a user and a system that provides menus and advice according to the user by linking a server that creates an exercise menu for the user to do exercise and advice for healthcare are described (see Patent Literature 2).

However, the technical proposals described in any of the above documents do not consider importance and necessity of individual inspection items and do not solve the present problem.

CITATION LIST

Patent Literature

Patent Literature 1: JP3144030B
Patent Literature 2: WO2002/051308

SUMMARY OF INVENTION

Technical Problem

In view of the problem that advice contents relating to health are complicated and difficult to understand, an object of the present invention is to provide a healthcare system that advises on an item having high importance and high necessity for each individual.

Solution to Problem

In order to solve the problem, a healthcare system according to the present invention is a healthcare system that determines and notifies advice contents according to importance of an item. The system measures each item related to health; calculates an evaluation value from the measured measurement value, the evaluation value being classified into evaluation classifications of a standard evaluation, a positive evaluation, and a negative evaluation; sets the importance of an inspection result for each measurement item; selects a predetermined number of items in descending order of a weight of the importance and in which the classification is the negative evaluation; generates an inspection result from contents of the evaluation classification of the selected item, and determines and notifies the advice contents according to the inspection result, the notification being performed on a printed matter or a screen of a mobile terminal.

In the present invention, a pattern is determined according to the inspection result, advice contents according to the pattern are determined and notified, and one pattern is determined for at least two evaluation results of different contents.

In the present invention, the weight of the importance is changed according to gender, age, and a pre-existing disease of the user.

In the present invention, a site, a URL of a video, or a matrix-type two-dimensional code according to the advice contents is added.

In the present invention, the weight of the importance is changed according to a history and change contents of a past inspection result.

In the present invention, an individual is identified by performing individual authentication of the user, and the measurement value and the evaluation value are collected and stored for each individual.

In the present invention, when the number of the items in descending order of weight of the importance and in which the classification is the negative evaluation does not reach the predetermined number, the inspection result including the items of the evaluation classifications of the standard evaluation and the positive evaluation is generated, and the advice contents are determined according to the inspection result.

Advantageous Effects of Invention

According to the healthcare system of the present invention, regardless of the number of measurement items, advice can be notified with respect to items having high importance and high necessity for each individual, and thus it is possible to provide accurate advice suitable for individual needs and to provide efficient and effective medical guidance.

BRIEF DESCRIPTION OF DRAWINGS

FIG. 2 is an individual weight-setting table of the healthcare system according to the present invention.

FIG. 3 is a relation table between measurement value and evaluation of the healthcare system according to the present invention.

FIGS. 4A and 4B are tables showing a selection example of an evaluation character string of the healthcare system according to the present invention.

FIG. 5 is a relation table between evaluation character string and pattern number of the healthcare system according to the present invention.

FIG. 6 is a relation table between pattern number and video sharing site of the healthcare system according to the present invention.

FIG. 9 is a modification of the relation table between evaluation character string and pattern number of the healthcare system according to the present invention.

DESCRIPTION OF EMBODIMENTS

A healthcare system according to the present invention is most characterized in that advice contents are determined and notified for each individual for an item having high importance and high necessity for each individual.
Hereinafter, embodiments of the healthcare system according to the present invention will be described with reference to the drawings.

Note that the healthcare system according to the present invention described below is not limited to the embodiments described below, and can be appropriately changed within the scope of the technical idea of the present invention, that is, within the scope of a device or a medium capable of exhibiting the same operation and effect, and within the scope of other configuration aspects thereof.

The present invention will be described with reference to FIGS. 1 to 9.

Figure 1:
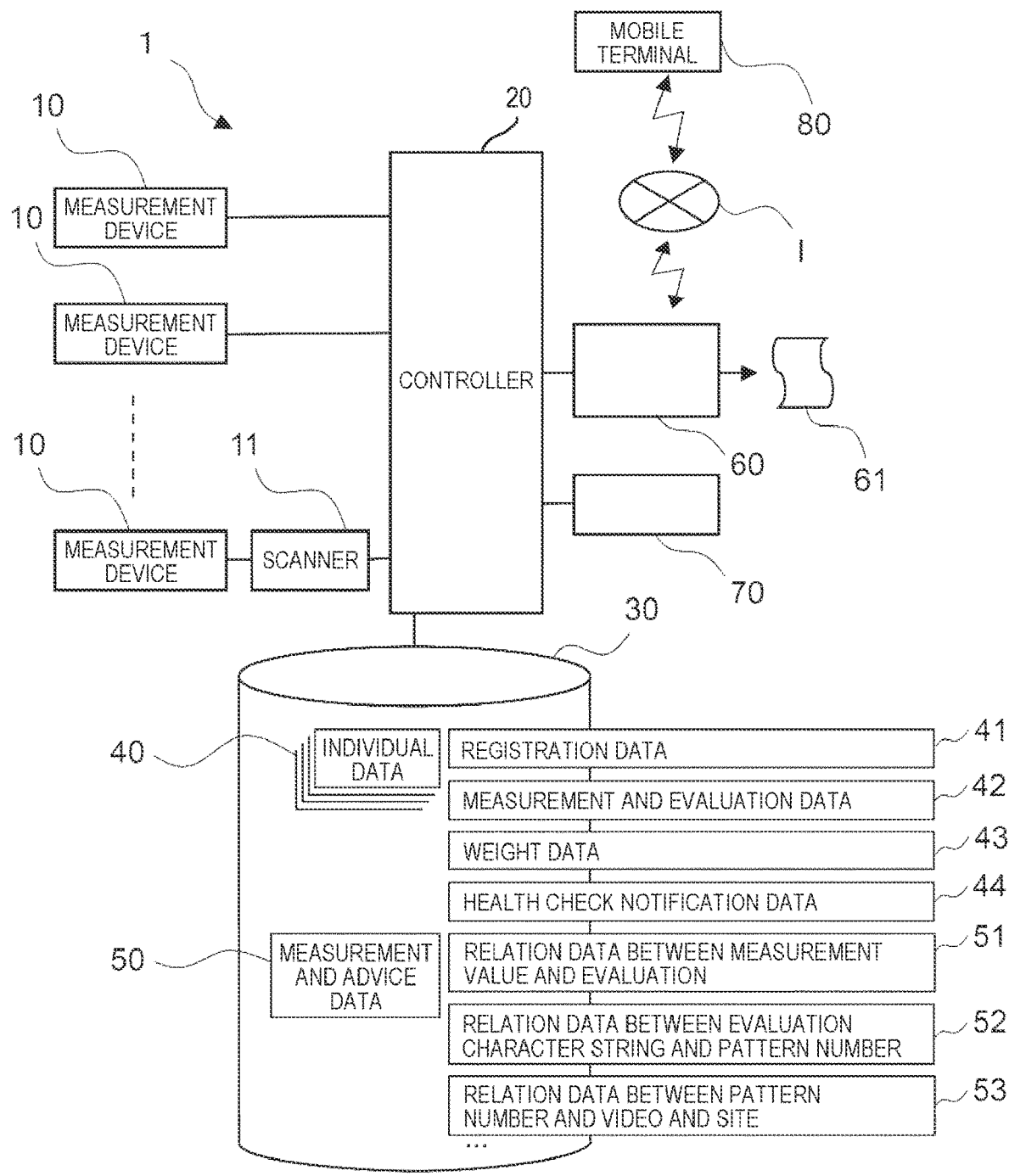
FIG. 1 is a system diagram of an embodiment of a healthcare system according to the present invention.
Figure 7A:
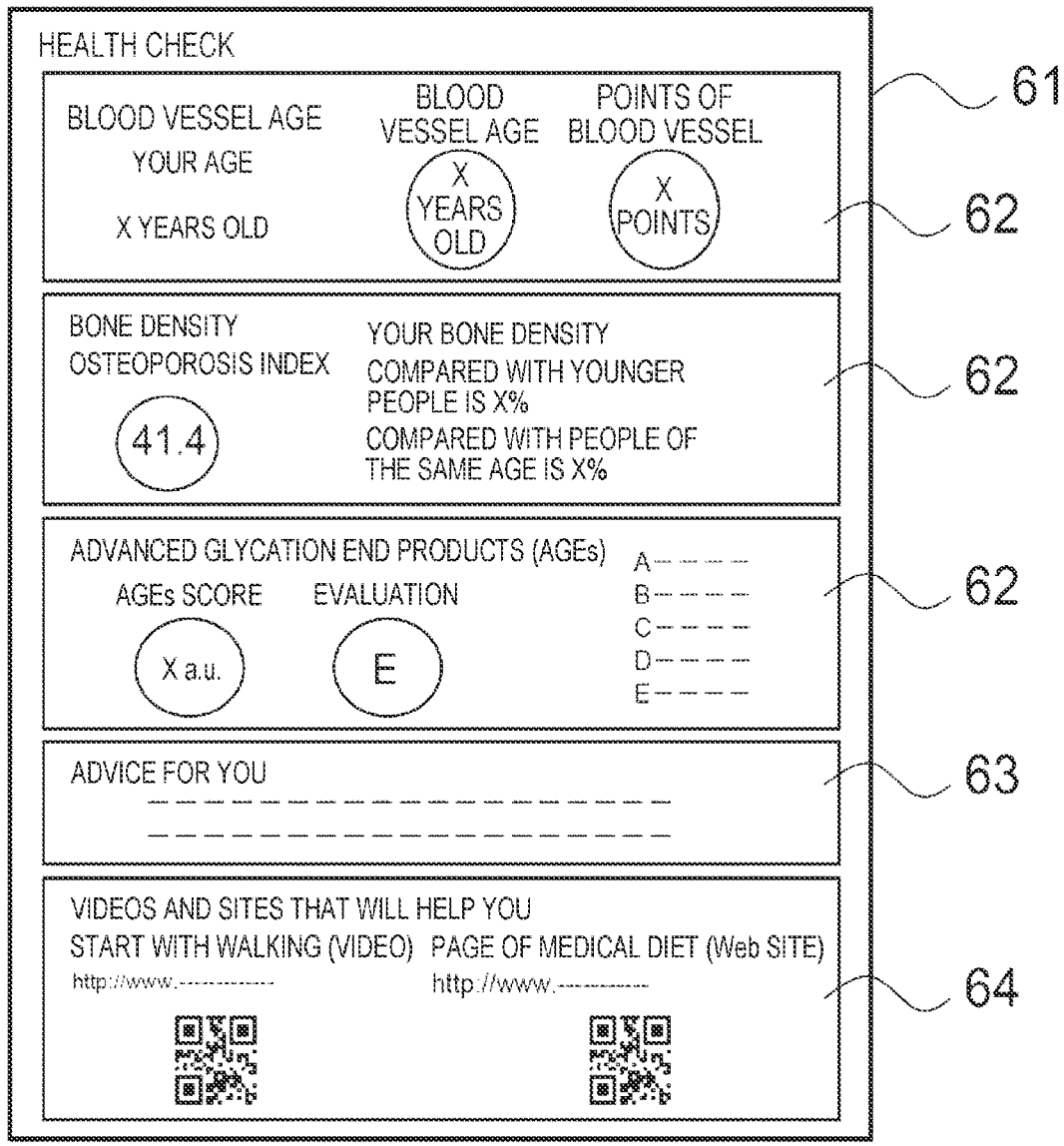
FIGS. 7A and 7B are examples of health check result output of the healthcare system according to the present invention.
Figure 7B:
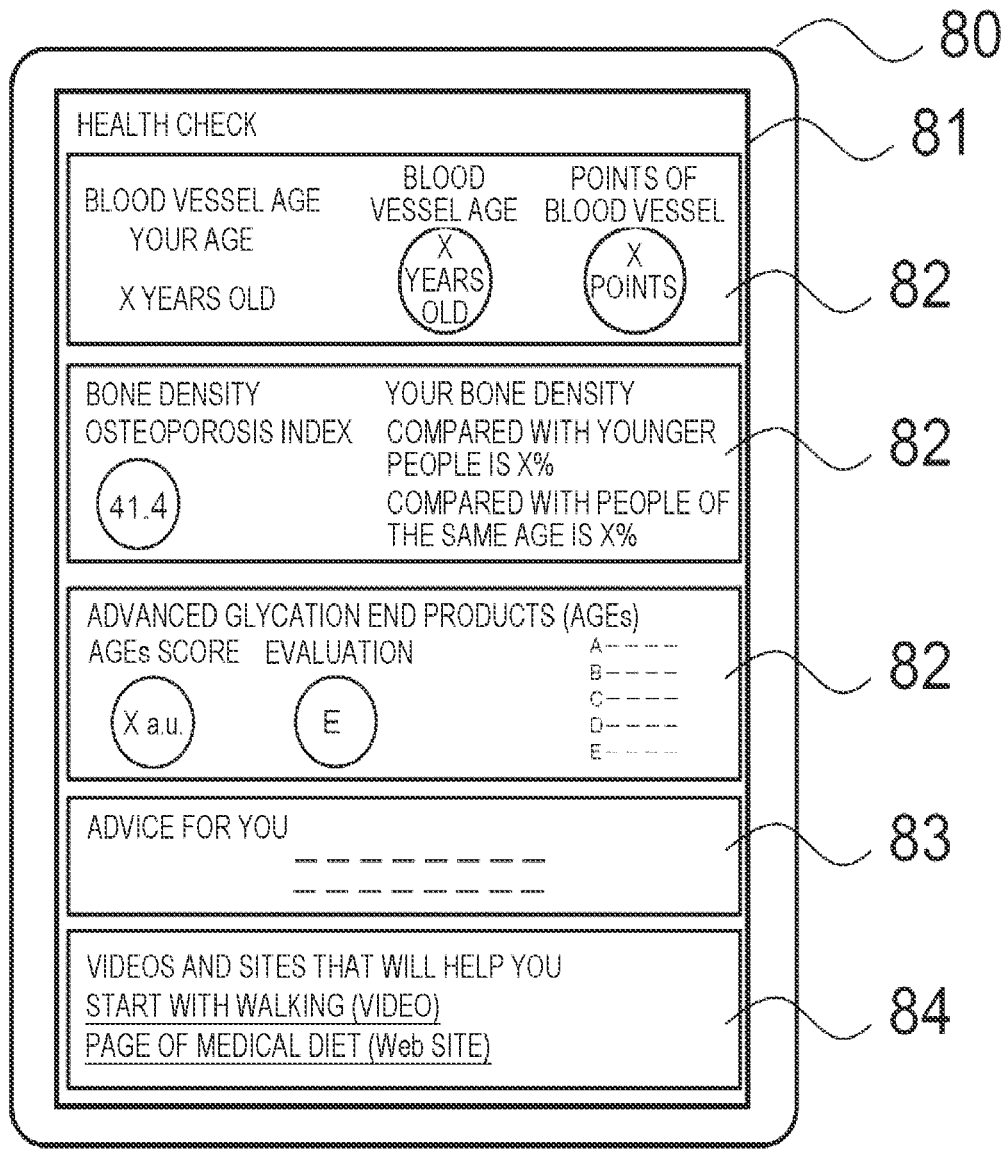
Figure 8:
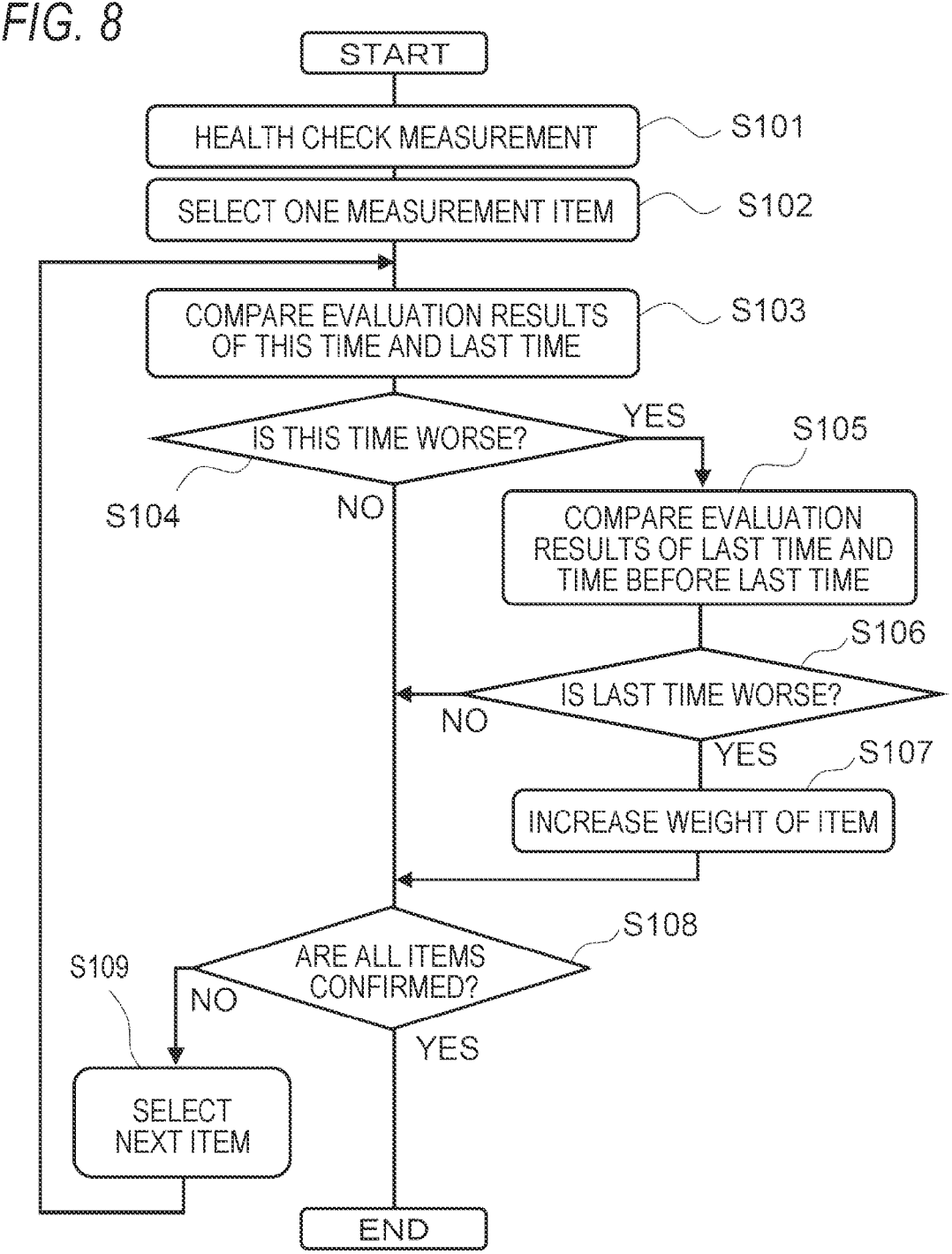
FIG. 8 is a flowchart for resetting a weight of the healthcare system according to the present invention.

FIG. 1 is a system diagram of an embodiment of the healthcare system according to the present invention. FIG. 2 is an individual weight-setting table of the healthcare system according to the present invention. FIG. 3 is a relation table between a measurement value and evaluation of the healthcare system according to the present invention. FIGS. 4A and 4B are tables showing a selection example of an evaluation character string of the healthcare system according to the present invention. FIG. 5 is a relation table between the evaluation character string and a pattern number of the healthcare system according to the present invention. FIG. 6 is a relation table between the pattern number and a video and a site of the healthcare system according to the present invention. FIGS. 7A and 7B are examples of health check result output of the healthcare system according to the present invention, in which FIG. 7A is an example of a case where the health check result is printed on paper and FIG. 7B is an example of a case where the health check result is output on a screen of a smartphone or the like. FIG. 8 is a flowchart for resetting a weight of the healthcare system according to the present invention. FIG. 9 is a modification of the relation table between the evaluation character string and the pattern number of the healthcare system according to the present invention.

A healthcare system 1 according to the present invention is a system in which measurement related to health of a user is performed in a pharmacy or the like, a value is evaluated, and appropriate advice is given to the user on the spot.

The healthcare system 1 includes a measurement device 10, a scanner 11, a controller 20, a database 30, an individual information input interface 70, and an evaluation result output interface 60. The measurement device 10 may include one or more.

The measurement device 10 is a measurement device that measures a health condition of a human body. The measurement device measures the human body and then transmits electronic data to the controller 20 in a wired or wireless manner. Alternatively, the measurement device 10 outputs a measurement result on paper or the like. As a format of the electronic data, for example, CSV format is suitable. This is because the CSV format is a common format and adopted by many devices. Examples of the measurement device 10 include a blood vessel age measurement device, a bone density measurement device, an advanced glycation end products (AGEs) measurement device, a body composition analyzer, a forgetfulness consultation, a skin age measurement device, and the like. The forgetfulness consultation may be verbally inspected by a person in charge.

The scanner 11 converts the results of the measurement device 10 whose measurement results cannot be directly transmitted to the controller 20 into image data. For example, in a blood pressure measurement device, the results are often printed on thermal paper. The printed result can be optically read and used as the image data. The image data is sent to the controller 20.

The controller 20 is a part that controls the entire system. The controller 20 receives the measurement result of the measurement device 10 and stores the measurement result in the database 30. The controller 20 digitizes the image data from the scanner 11 by an OCR library and stores the image data in the database 30.

The controller 20 stores individual data 40 input from the individual information input interface 70 in the database 30. The controller 20 collates an ID and the like input by the individual information input interface 70 with the data of the database 30 and processes the ID and the data.

The controller 20 generates health check notification data 44 using the individual data 40 and measurement and advice data 50, and outputs the health check notification data 44 by the evaluation result output interface 60. The output health check result is notified to the individual as a paper medium or as a screen of a mobile terminal 80 via an Internet I.

The database 30 is a main part of the present invention. The database 30 is a cloud server. Since the database 30 is a cloud server, data can be collectively managed even when the user uses this system at a plurality of pharmacies.

The database 30 is roughly divided into the individual data 40 and the measurement and advice data 50. The individual data 40 is data related to an individual who undergoes health checks, and includes registration data 41, measurement and evaluation data 42, weight data 43, and health check notification data 44.

The registration data 41 is registration data of the individual. The registration data 41 includes the ID, a password, a name, an address, a telephone number, a birth date, gender, age, a pre-existing disease, and the like. The data is input at the time of an initial health check. The data is modified as necessary.

The measurement and evaluation data 42 is evaluation data obtained from a measurement value and an evaluation value in the inspection. A health condition is determined according to values of the evaluation data. Past data is also stored as a history.

The weight data 43 is data for determining a priority of each individual for each inspection item. The higher a weight is, the higher the priority is. The weight is a value according to the age, the gender, the pre-existing disease, and the like. In the health check result, advice corresponding to a higher item of the weight is given.

The health check notification data 44 is advice or the like based on the evaluation result. The health check notification data 44 includes the evaluation result of each item, advice about a main inspection item, a related video, a Web site, an introduction of a medical institution, and the like.

A graph or a radar chart may be used for the evaluation of each item.

The measurement and advice data 50 is a data group such as an evaluation standard at the time of measurement in the inspection, an advice index for the result, and the like. The measurement and advice data 50 includes relation data 51 between measurement value and evaluation, relation data 52 between evaluation character string and pattern number, and relation data 53 between pattern number and video sharing site, which are basically fixed values.

The relation data 51 between measurement value and evaluation is data showing a relation between the measurement value and the evaluation (FIG. 3 and T20). The relation data 51 between measurement value and evaluation is for determining a threshold value, an initial value, and a classification value of each evaluation. The evaluation is divided into a negative evaluation, a standard evaluation, and a positive evaluation.

The relation data 52 between evaluation character string and pattern number is data showing a relation between a pattern of the advice index and a character string generated by selecting a predetermined number of items in descending order of a weight and in which the classification is the negative evaluation among the evaluations (FIG. 5 and T30). The relation data 52 between evaluation character string and pattern number is for determining the pattern number serving as the advice index by limiting to items having high importance and the negative evaluation among the inspected items. By determining the advice index, a guideline of guidance to the user is also uniquely determined.

The relation data 53 between pattern number and video sharing site is data in association with advice, a comment, the video, the site, and the like corresponding to the pattern number which is the advice index (FIG. 6 and T40). The advice is automatically generated corresponding to the pattern number. The comment is input by a registered dietitian and a pharmacist. The advice also includes contents of a question from the user. As the video, for example, a video of exercise therapy, a video of medical diet, and a video of drug explanation are set. As the site, a site that leads to improvement by the medical diet, a site that leads to improvement by the exercise therapy, and a site that introduces specialized medical institutions near where the user lives are set.

In addition, a site that introduces healthy foods and healthy goods may be set.

The evaluation result output interface 60 is apart that outputs health check result output 61 to the user. Output contents include columns of the measurement value, an evaluation value, the advice, the video, and the like. It is possible to select, according to desire of the user, a method of printing on paper and a method of sending information to the mobile terminal 80 such as a smartphone and confirming the information by the user on the mobile terminal 80.

The individual information input interface 70 is apart in which the information is input by the user. The individual information input interface 70 inputs the name, the address, the telephone number, the age, the gender, the pre-existing disease, and the like at the initial health check, and issues an ID and a password for user registration and user access.

In subsequent health checks, the individual will be identified by the ID and the password. The inspection result of the health check is recorded in the individual data 40 of the database 30. In this regard, it is also possible to adopt a method of performing individual authentication in initial registration and subsequent registrations by using an IC card or a mobile terminal in which various individual information is registered and reading the individual information by a reading device. Alternatively, it is also possible to adopt a method of performing biometric authentication registration at the time of initial registration and a method of identifying the individual by biometric authentication in subsequent registration.

The mobile terminal 80 is a terminal used by an individual user, and is mainly a smartphone. The mobile terminal 80 is connected to the evaluation result output interface 60 via the Internet I and receives each piece of information. Although not shown, a question or the like to the pharmacy can be transmitted from the mobile terminal 80 to a system 7.

Flow of Health Check Measurement

A rough flow of the health check measurement will be described.

First, the user inputs the name and the like of the user per se through the input terminal as the individual information input interface 70 and acquires the ID and the password.

Next, the user performs each measurement, the measurement result is converted into data and is taken into the database 30. The measurement result is compared with predetermined reference data in the database 30.

At this time, the measurement result may be converted into graphs. The data output from each health measurement device corresponds to each individual, and a current position of data of the individual can be grasped by being compared to the reference data.

Next, when the measurement result falls below a standard value, each piece of information is provided by the health check result output 61. It is sufficient to simply notify the user that the measurement result falls below the standard value, but in such a case, the user often does not know a specific method for improvement.

For example, by guiding the user to a site that leads to improvement through the medical diet or to a site that leads to improvement through exercise therapy, the user can easily take a specific action. It is also conceivable to guide the user to a pharmacotherapy introduction site. It is also possible to guide the user to a site that introduces healthy foods and healthy goods.

In addition, a medical institution is introduced. The user can be improved by treatment by a medical specialist or the like. By utilizing position information of a smartphone or the like, it is possible to guide the user to a site that introduces a specialized medical institution near where the user lives.

In this way, it is possible to provide a service that is performed in one stop from the measurement to the treatment.

Description of Each Data

Each data will be described. T10 is a table for setting individual weights (FIG. 2). Weight values are set to be 100% in total. An item having a larger weight value is processed as an item important for the user. There is also a method of allowing the user to set the weight, but the user cannot easily set the weight unless the user has specialized knowledge. Therefore, a weight suitable for the user is set by changing the weight of each item according to the age, the gender, the pre-existing disease, or the like of the user.

For example, bone density is more likely to decrease in women than in men. In addition, the bone density tends to decrease with age. In addition, since women are more concerned about skin age than men, the importance of the skin age is higher for women.

For example, in the case of men in their 50s, setting is made as in a row of T11. As men in their 50s are middle-aged and older, a weight of blood vessel age associated with atherosclerosis is increased to 30%. Next, a weight of the bone density is increased to 25%. A weight of advanced glycation end products (AGEs) and a weight of body composition analysis are set to 20% and 15% respectively, and a weight of forgetfulness and a weight of skin age are set to 5%, which are the lowest weight.

Although this table does not take pre-existing diseases into consideration, tables adjusted according to presence or absence of diabetes, obesity, and the like are also prepared.

Next, a relation table between measurement value and evaluation will be described (FIG. 3 and T20).

The evaluation value with respect to the measurement value is set for each inspection item. The leftmost column of the table is the inspection item. The next column is an inspection item identification symbol. The inspection item identification symbol is a symbol uniquely determined for each inspection item and is determined when the pattern number is determined.

The next column is a weight for each inspection, and the weight is higher for an item that is important for the user. The next column shows contents of the evaluation. The next column of a distributed point-corresponding character string is a part in which the evaluation with respect to the measurement value and a character string corresponding to the evaluation are determined. In the evaluation, the negative evaluation is set to three levels, the standard evaluation is set to one level, and the positive evaluation is set to two levels. The levels may be appropriately increased or decreased depending on the contents of the inspection item.

The character string set here is combined with the inspection item identification symbol to determine the pattern number.

As an example, the item of the blood vessel age will be described. An example of men in their 50s is shown. The inspection item identification symbol is A, and the weight is set by a row of T11 in T10 and is 30%. A determination item is a score out of 100 points, and a score of less than 40 points is the negative evaluation. The negative evaluation is classified into three classifications of 19 points or less, 20 to 29 points, and 30 to 39 points. The standard evaluation has one classification of 40 points to 59 points. The positive evaluation is classified into two classifications of 60 points to 79 points and 80 points to 100 points.

The character string corresponding to each classification is assigned. For example, in the case of 19 points or less, the character string is a. When the inspection result of the blood vessel age is 19 points or less, Aa is generated as the result.

For other inspection results, similarly, a scheduled character string is generated from the inspection item identification symbol and the evaluation classification.

Although it is also possible to generate the character string for all inspection items and advise along the character string, there is a possibility that an amount of advice becomes enormous, and a ratio of unimportant advice increases for the user in many cases. Therefore, in order to advise important items for the user, a method of selecting a predetermined number of items in descending order of weight and in which the classification is the negative evaluation will be described. Here, the predetermined number is assumed to be 3.

A specific example will be described using FIGS. 4A and 4B. In the evaluation, apart surrounded by a thick frame is the evaluation result. The weight is assumed to be a high-weight item from the upper row.

In FIG. 4A, when three items in descending order of weight and having the negative evaluation are selected, the blood vessel age, the bone density, and the AGEs are selected. The character string as the evaluation result of this case is AaBgCm.

In FIG. 4B, similar to FIG. 4A, when three items in descending order of weight and having the negative evaluation are selected, since the AGEs is standard in the evaluation and is not applicable, the blood vessel age, the bone density, and the body composition analysis are selected. The character string as the evaluation result of this case is AaBiDs.

Next, an advice pattern setting table will be described (FIG. 5 and T30).

A character string AaBgCm and the like of the evaluation result is generated by adding a predetermined condition to the evaluation result of T20 as described above. A pattern number is a number corresponding to the evaluation result, and the advice contents are determined according to this pattern number.

For example, in the case of a row of T31, the pattern number corresponding to the character string AaBgCm of the evaluation result is 1, and the advice contents are contents of PAY ATTENTION TO BLOOD VESSEL AGE, PAY ATTENTION TO BONE DENSITY, and PAY ATTENTION TO AGEs.

Basically, the character string and the pattern of the evaluation result have a one-to-one relation. However, with respect to elements having relatively low importance, there is a case where the advice per se is not greatly affected even if the patterns are collected. For example, in a row of T32 and a row of T33, the negative evaluations of AGEs indicated by C are different in moderate and mild. The advice contents are focused on the blood vessel age and the bone density. Therefore, when the advice contents for moderate and mild AGEs are combined, the advice contents can be simplified and the contents of the explanation to the user can be clarified.

Therefore, in T30, 12 pattern numbers correspond to 27 character strings by combining relatively mild items.

In addition, when three items in descending order of weight and having the negative evaluation are selected, the number of items having the negative evaluation may be less than three, depending on search results. In this case, the condition may be changed, and an item having the standard evaluation or the positive evaluation may be entered.

For example, the advice pattern setting table of the case where the negative evaluation is only the blood vessel age is indicated by T50 in FIG. 9. T50 is the case where the evaluation of the blood vessel age is a negative evaluation of any one of Aa, Ab, and Ac, the evaluation of the bone density is any one of standard Bj and positive evaluations Bk and Bl, and the evaluation of AGEs is any one of standard Cp and positive evaluations Cq and Cr.

For example, when being represented by AaBjCp, the evaluation character string corresponds to a row of T51, and the pattern is 101. In this case, the advice is to PAY ATTENTION TO BLOOD VESSEL AGE and BONE DENSITY STANDARD since the bone density is a standard numerical value. For example, the advice is that "bone density is an age-appropriate value. Continue to eat a diet that is conscious of calcium and to take light exercise".

Since the AGEs is a standard numerical value, the advice corresponds to AGEs STANDARD. For example, the advice is that "AGEs is a standard value. Continue to eat a balanced diet and exercise regularly".

Next, a relation table between a video and a site corresponding to a pattern number will be described (FIG. 6 and T40).

Since the pattern number is sorted according to the inspection result of the user, it is possible to advise according to the health condition of the user by setting a video and a site corresponding to the pattern number and advise to the user.

For example, in response to a decrease in the bone density, an exercise video that maintains the bone density is considered.

In addition, regarding the medical diet, a video commentary and a video of a message by a registered dietitian are considered according to the stage of the measurement result. At this time, the user may be guided to a video in good, slightly carelessness, carelessness, immediate treatment, or the like in stages.

In addition, the user may be guided to a video of drug explanation by a pharmacist.

As an example, a row of T41 is a pattern 1, and the inspection result is that PAY ATTENTION TO BLOOD VESSEL AGE, PAY ATTENTION TO BONE DENSITY, and PAY ATTENTION TO AGEs, and thus the video is set to general life guidance, and the site is set to introduction of overall medical diet site.

In this way, by introducing the video and the site according to the health condition, it is possible to easily confirm contents of the guidance of the user.

Similarly, introduction of a medical institution may be set according to the inspection result.

A method of notifying the user of the health check result will be described (FIGS. 7A and 7B).

The inspection result is notified to the user from the evaluation result output interface 60. The method of notification includes a method of printing the inspection result and the like on paper and handing the paper to the user and a method of transmitting data to the mobile terminal 80 of the user via the Internet I and confirming the contents on a display screen 81 of the mobile terminal 80 by the user.

An example of notification on paper will be described along FIG. 7A.

In the health check result output 61, a health check evaluation result field 62, an advice field 63, and a video introduction field 64 are described. In the health check evaluation result field 62, each inspection item name, inspection result, and evaluation result are described in a user-friendly form for each inspection item.

The health check evaluation result field 62 may be simply represented by a numerical value or may display a graph for comparing the standard value and the measurement result, a comparison based on a radar chart of an excellent model and a personal numerical value, an evaluation based on a radar chart of muscle mass by body composition analysis, and a change in the measurement result in time series as necessary.

The advice field 63 describes advice for the inspection result. The advice field 63 is advice contents corresponding to the pattern number and is advice contents according to the importance of the item for the user. In addition, comments by a registered dietitian and a pharmacist and answers to previous questions from the user are also included.

By the advice field 63, the user can receive advice for an item having high importance and high necessity for advice in the inspection result.

The video introduction field 64 is a part of introducing a video or a Web site to be referred to by the user from the inspection result. Since the video and the site are designated by the relation table between pattern number and video sharing site, the video and the site can be accurately set to correspond to the inspection result of the user. For example, a video and a site that connect to the exercise therapy (sports gym, physical therapist, and occupational therapist), the medical diet (registered dietitian), the pharmacotherapy (pharmacist), consultation recommendations for medical institutions, and the like are effective.

By placing a simple introduction of a video and a site, a URL, a matrix-type two-dimensional code represented by a QR code (registered trademark), and the like, the user can easily confirm a reference video sharing site.

Similarly, a URL and a matrix-type two-dimensional code of a related medical institution may be placed.

An example in which a notification is made to the mobile terminal 80 will be described with reference to FIG. 7B.

The health check result is displayed on the display screen 81 of the mobile terminal 80. The health check evaluation result field 82 and the advice field 83 are substantially the same as those in the case of paper. The health check evaluation result field 82 may be arranged according to the size or the like of the screen. Since a video and a site can be displayed on the mobile terminal 80 in the video introduction field 84, the URL is pasted on the screen, and the user clicks the URL, so that the video and the site can be viewed for the purpose.

In this way, the user can easily confirm the reference video and the like.

Adjustment of Weight

The weight indicating the inspection importance of the user is determined by the weight data 43, and the weight data 43 is determined according to the individual weight-setting table. However, if there is an item that gradually deteriorates with respect to a specific inspection item during repetition of the inspection of the health check, the weight should be increased in the meaning of calling attention to the user.

As a method of changing the weight from a history of the inspection, there is a method in which individual items are checked by a relatively simple program and the weight is changed or a method in which Artificial Intelligence (AI) learning is performed based on inspection data of many people and the weight is changed.

The method of changing the weight by a relatively simple program will be described along FIG. 8. Here, it is assumed that health checks are performed twice or more in the past.

A health check measurement is performed (S101). Each measurement and evaluation are performed by a predetermined method, and the measurement result and the evaluation result are stored in the database 30.

One stored item is selected (S102). For that item, evaluation results of this time and the last time are compared (S103). It is determined whether the evaluation result of this time is worse than that of the last time (S104). When the evaluation result of this time is worse than that of the last time, the process proceeds to S105. Next, the evaluation result of the last time is compared with that of the time before the last time (S105). It is determined whether the evaluation result of the last time is worse than that of the time before the last time (S106). When the evaluation result of the last time is worse than that of the time before the last time, the process proceeds to S107. Regarding this item, the evaluation results are getting worse consecutively from the time before the last time, the last time, and this time. Therefore, the weight is increased, the importance is increased, and a priority of advice to the user is increased (S107).

It is checked whether all items are confirmed (S108). If not, the next item is selected (S109), the process is returned to S103, and a state of deterioration is confirmed.

By performing this process for each inspection, it is possible to advise according to continuous changes in the health condition of the user.

The method of adjusting the weight by AI learning will be described. First, the AI is caused to learn inspection items continuously inspected by many subjects, measurement results, evaluation results, and weights thereof, age, gender, and pre-existing disease of the subjects. Based on the data, a feature of the individual user and a model close to the inspection result are estimated. In response to this, a recommended weight is calculated, and the weight of the user is changed. By appropriately performing AI learning, different determinations can be made depending on age, gender, and pre-existing disease with respect to the variation in inspection contents, and a weight more suitable for the health condition of the user can be set.

In this way, according to the healthcare system of the present invention, regardless of the number of measurement items, advice can be notified with respect to items having high importance and high necessity to advise for each individual, and thus it is possible to provide efficient medical guidance.

In addition, it is possible to give more accurate advice by sorting which advice is to be guided by an arrangement of character strings instead of numerical values.

In general, the healthcare system according to the present invention not only simply notifies the user of the health check result, but also provides accurate advice and guidance with respect to the items having high importance and necessity for each individual by attaching, based on the health check result, various kinds of contents such as advice by a pharmacist or a registered dietitian, introduction of an exercise effective for symptom improvement in cooperation with a sports gym, measures against stiff shoulders and low back pain in cooperation with a physical therapist or an occupational therapist, and introduction of On-the-counter (OTC) or healthy foods by a pharmacist or a registered dietitian.

In addition, various following functions can be added such as a function of linking with a medication notebook (confirmation of medication information), an advice function to a person having a basic disease (registration of basic disease information), a monitoring support function (sharing a measurement result with a family member in a remote place), introduction of a medical institution (guidance of a neighboring specialized medical institution according to a symptom by a GPS function of a mobile terminal), comparison with an average value by a radar chart, a reminder function (prompting re-measurement after a certain period of time elapsed from measurement), and Q & A (automatic response) relating to a method of using a drug based on an attached document of a pharmaceutical product, and thus the user can perform follow-up in a multifaceted manner.

As other functions, it is also possible to add functions such as introduction of OTC, discount coupon, advertisement of sponsor product, matching of OTC (function of inputting disease condition and pre-existing disease and guiding appropriate OTC), order of a placement drug (order on an application and delivery to home of a user), and the like. Furthermore, by adding a confirmation tool of a congestion situation or an inventory status of a pharmacy, a point in cooperation with an eco-bag or other ecological actions, providing a brain training tool (Sudoku, crosswords, and the like) and daily topics (providing topics that go back in the past and what happened on that day, such as "xx month and xx day was 19XX years, XX day"), and contents such as contents for people who are dieting goals (providing tasks, giving points for achieving goals, ranking functions among users, and the like), it is also possible to adopt a mode in which the use of the present system is promoted.

INDUSTRIAL APPLICABILITY

In the healthcare system according to the present invention, as a method of improving convenience of a health check system, it is understood that industrial availability is high.

REFERENCE SIGNS LIST

1: healthcare system
10: measurement device
11: scanner
20: controller
30: database
40: individual data
41: registration data
42: measurement and evaluation data
43: weight data
44: health check notification data
50: measurement and advice data
51: relation data between measurement value and evaluation
52: relation data between evaluation character string and pattern number
53: relation data between pattern number and video sharing site
60: evaluation result output interface
61: health check result output
62: health check evaluation result field
63: advice field
64: video introduction field
70: individual information input interface
80: mobile terminal
81: display screen
82: health check evaluation result field
83: advice field
84: video introduction field
I: Internet

The invention claimed is:
1. A healthcare system configured to determine and notify advice contents according to importance of an item, comprising:
a database;
a controller;
an output interface; and
a measurement device,
wherein
the measurement device is configured to:
measure data related to health of a user for each inspection item; and
transmit the measured data to the controller,
the controller is configured to:
transmit and store the data to the database;
calculate an evaluation value from the measured data by using a table in the database;

classify the evaluation value into evaluation classifications of a standard evaluation, a positive evaluation, and a negative evaluation;

set an importance of an inspection result for each measurement item;

select a predetermined number of items in descending order of a weight of the importance and in which the classification is the negative evaluation;

generate an inspection result from contents of the evaluation classification of the selected item; and determine the advice contents according to the inspection result, the output interface is configured to:

transmit guidance to a medical institution, according to a Global Positioning Satellite (GPS) function of a mobile terminal and the advice contents, to the mobile terminal via an internet, and the controller is further configured to:

determine a pattern according to the inspection result;

determine and notify advice contents according to the pattern;

determine one pattern for at least two evaluation results of different contents, generate an evaluation character string based on selecting a predetermined number of the items in descending order of weight of the importance and in which the classification is the negative evaluation; and combine the evaluation character string with an item identification symbol to determine a pattern number corresponding to the pattern.

2. The healthcare system according to claim 1, wherein the controller is further configured to change the weight of the importance according to gender, age, and a pre-existing disease of the user.

3. The healthcare system according to claim 1, wherein the controller is further configured to add a site, a URL of a video, or a matrix-type two-dimensional code according to the advice contents.

4. The healthcare system according to claim 1, wherein the controller is further configured to change the weight of the importance according to a history and change contents of a past inspection result.

5. The healthcare system according to claim 1, wherein the controller is further configured to identify an individual by performing individual authentication of the user, and the data and the evaluation value are collected and stored for each individual.

6. The healthcare system according to claim 1, wherein when a number of the items in descending order of weight of the importance and in which the classification is the negative evaluation does not reach the predetermined number, the controller is further configured to:

generate the inspection result including the items of the evaluation classifications of the standard evaluation and the positive evaluation; and determine the advice contents according to the inspection result.

7. The healthcare system according to claim 1, wherein the controller is further configured to change the weight of the importance according to gender, age, a pre-existing disease of the user, and a history and change contents of a past inspection result.

* * * * *